United States Patent [19]

Toge

[11] Patent Number: 5,134,445
[45] Date of Patent: Jul. 28, 1992

[54] SAMPLE INSPECTING METHOD AND APPARATUS

[75] Inventor: Yoshiyuki Toge, Yokohama, Japan

[73] Assignee: Canon Kabushiki Kaisha, Tokyo, Japan

[21] Appl. No.: 476,771

[22] Filed: Feb. 8, 1990

[30] Foreign Application Priority Data

Feb. 14, 1989 [JP] Japan .................................. 1-35345
Feb. 14, 1989 [JP] Japan .................................. 1-35346
Feb. 14, 1989 [JP] Japan .................................. 1-35347

[51] Int. Cl.$^5$ ..................... G01N 15/02; G01N 21/85
[52] U.S. Cl. ................................. 356/336; 356/410; 356/39; 356/246
[58] Field of Search .......................... 356/335-343, 356/410, 441, 318, 440, 39, 73, 72, 244, 246; 250/574, 575, 461.2, 227

[56] References Cited

U.S. PATENT DOCUMENTS

| | | | |
|---|---|---|---|
| 3,236,602 | 2/1966 | Isreeli | 356/39 |
| 3,418,053 | 12/1968 | Pelaoin | 356/410 |
| 3,518,008 | 6/1970 | Skeggs | 356/246 |
| 3,518,009 | 6/1970 | Shamos et al. | 356/410 |
| 3,604,814 | 9/1971 | Skeggs | 356/410 |
| 3,697,185 | 10/1972 | Kassel et al. | 356/410 |
| 3,804,593 | 4/1974 | Smythe et al. | 356/410 |
| 3,909,136 | 9/1975 | Thomas | 356/410 |
| 4,606,631 | 8/1986 | Anno et al. | 356/338 |

*Primary Examiner*—Richard A. Rosenberger
*Assistant Examiner*—Hoa Pham
*Attorney, Agent, or Firm*—Fitzpatrick, Cella, Harper & Scinto

[57] ABSTRACT

A sample inspecting method and apparatus serially accumulates a plurality of liquids into a liquid path. The liquid path is pressurized to supply the accumulated liquids to an inspection station, wherein particles of selected liquids are inspected. A gas can be incorporated between each liquid and detected to discriminate between different sample liquids and washing liquids.

14 Claims, 8 Drawing Sheets

SAMPLE INSPECTING METHOD AND APPARATUS

BACKGROUND OF THE INVENTION

1. Field of the Invention

This invention is applied chiefly to a sample measuring apparatus such as a flow cytometer, and relates to a sample inspecting method of supplying a sample to an inspecting portion and inspecting the sample in the inspecting portion, and an apparatus therefor.

2. Related Background Art

In a prior-art sample inspecting method and apparatus applied to a particle measuring apparatus or the like, there is usually practised a method of once sucking sample liquid such as a prepared blood sample into the apparatus, collecting it into a sample loop comprised of a fine tube, extruding it by extrusion liquid and supplying it to an inspecting portion.

When the operator brings a test tube containing sample liquid therein to the position of a sample suction tube exposed to the exterior of the apparatus and causes the sample liquid to be sucked by the sample suction tube, measurement is started automatically or by a measurement starting switch. After the measurement is completed and the interior of a water channel is washed to thereby restore the initial state, sample liquid is likewise sucked from another sample liquid test tube and measurement is repeated.

However, in the prior-art sample inspecting method and apparatus, when a plurality of sample liquids are to be measured, only after the measurement of a sample liquid has been completed is it possible to suck the next sample liquid. Consequently, it has been necessary for the operator to always stand by the apparatus and frequently carry out the sample sucking work. However, the waiting time for measurement is wasted time to the operator, and this has meant a low time efficiency to the operator.

Also, an auto sampler has been large-scale in construction, and this has led to the problems of complexity and expensiveness.

SUMMARY OF THE INVENTION

The present invention has as its object the provision of a sample inspecting method capable of supplying a plurality of kinds of samples continuously by a simple construction and inspecting them and an apparatus therefor.

DESCRIPTION OF THE PREFERRED EMBODIMENTS

Figure 1:
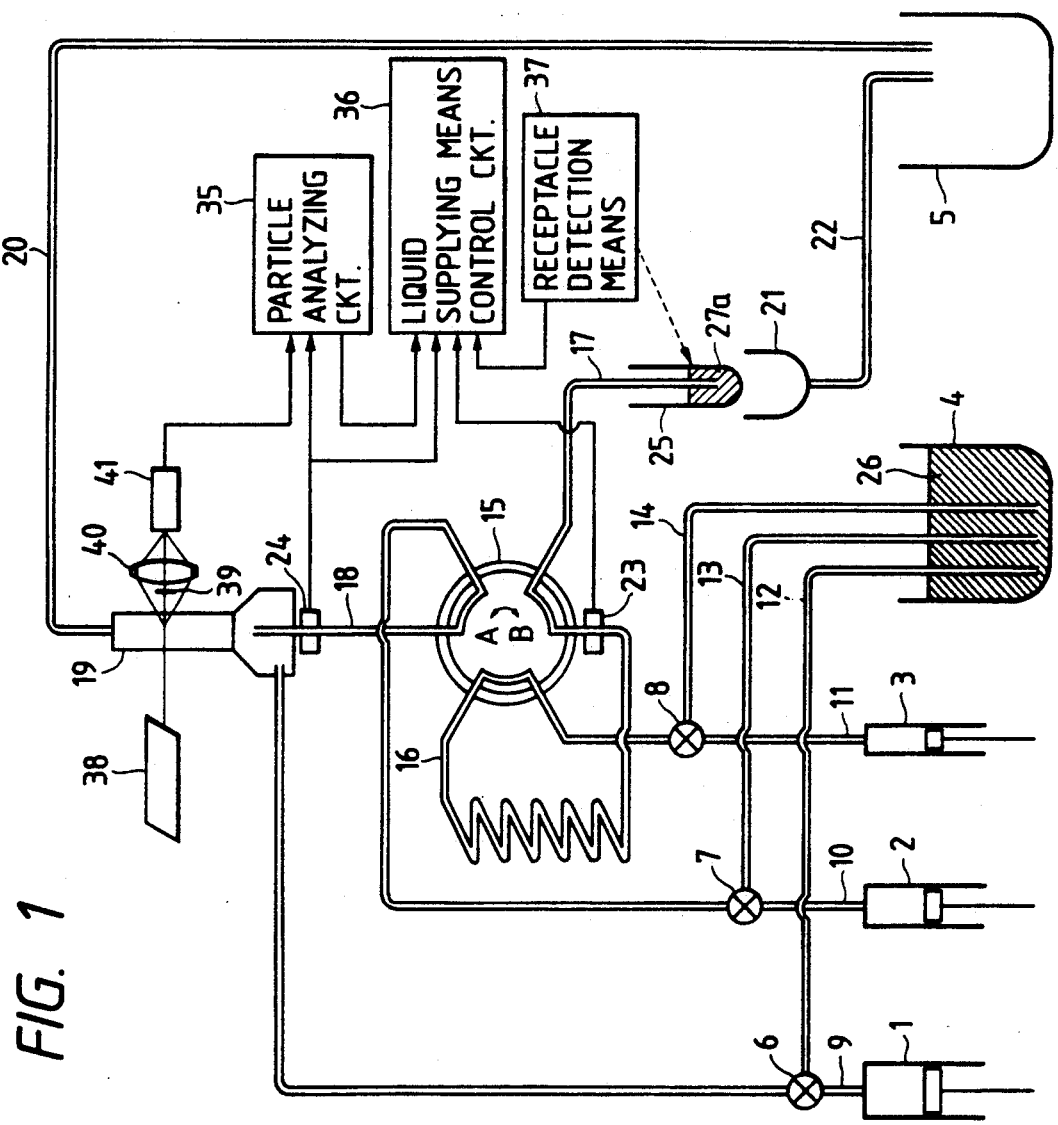
FIG. 1 is a schematic illustration of an embodiment of the present invention.

FIG. 1 shows the construction of an embodiment in which the present invention is applied to a flow cytometer. In FIG. 1, the reference numeral 1 designates a sheath pump, the reference numeral 2 denotes a washing pump, and the reference numeral 3 designates a sample pump. Each of these is comprised of a syringe driven by a motor. These pumps 1, 2, 3, and 3-port values 6, 7, 8 and a 6-port value 15 which will be described later are controlled by a liquid supplying means control circuit 36. A tube 9 is connected to the sheath pump 1, and the other end thereof is connected to the sheath liquid inlet port of a flow cell 19. The 3-port valve 6 is provided halfway of the tube 9 and a tube 12 is connected to the 3-port valve 6, and the other end of the tube 12 is immersed in sheath liquid 26 having the washing function which is accumulated in a sheath liquid receptacle 4. Tubes 10 and 11 are connected to the washing pump 2 and the sample pump 3, respectively, and the other ends of these tubes are connected to the 6-port valve 15. The 3-port valves 7 and 8 are provided halfway of the tubes 10 and 11, respectively, and tubes 13 and 14 are connected to the 3-port valves and 8, respectively, and the other ends of the tubes 13 and 14 are immersed in the sheath liquid 26 in the sheath liquid receptacle 4 having the washing function. A sample suction tube 17, the opposite ends of a sample loop 16 for collecting sucked sample liquid 27a therein and a tube 18 for supplying the sucked sample liquid 27a to the sample inlet port of the flow cell 19 are connected to the 6-port valves 15. The sample loop 16 and the tube 18 are made of a transparent material, and sensors 23 and 24 which are gas detectors in the tubes are provided near the 6-port valve 15 on that side of the sample loop 16 which is connected to the sample suction tube 17 and in the portion of the tube 18 which is near the flow cell 19. The output signals of these sensors are connected to a particle analyzing circuit 35 and the liquid supplying means control circuit 36.

Figure 2A:
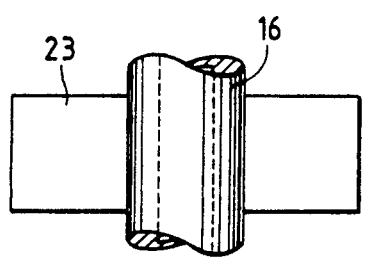
FIGS. 2A and 2B are detailed views of gas detecting sensors.
Figure 2B:
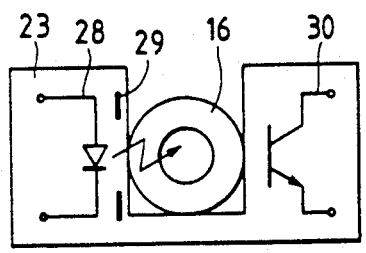

FIG. 2 shows the details of the sensors 23 and 24. Each sensor is comprised of an LED 28, a slit 29 and a photoelectric element 30 with a transparent tube 16 or 18 interposed therebetween. In this construction, the degree to which light is transmitted is varied by the difference in refractive index between substances in the tube and therefore, whether the interior of the tube in the sensor portion is air or sample liquid can be judged.

A laser source 38 is disposed toward the inspecting portion in the flow cell 19, and sample liquid such as a blood sample is converged into a thin stream while being wrapped in the form of a sheath in the sheath liquid, and a laser beam emitted from the laser source 38 is applied to fine particles such as blood corpuscle cells in the sample liquid flowing one particle by one through the inspecting portion, and scattering of light is caused by the fine particles. The light is directly removed by a stopper 39 provided at a position opposed to the laser source 38 with the flow cell 19 interposed therebetween, and forwardly scattered light condensed by a lens 40 positioned rearwardly of the stopper 39 is photometered by a photodetector 41. The output of the photodetector 41 is connected to the particle analyzing circuit 35. Although not shown, an optical system for photometering sideways scattered light and fluorescence is provided in a direction perpendicular to the plane of the drawing sheet. These photometering outputs are also connected to the particle analyzing circuit 35.

Measured waste liquid passed through the flow cell 19 is discarded into a waste liquid receptacle 5 through a waste liquid tube 20 connected from the flow cell 19 to the waste liquid receptacle 5. The reference numeral 25 designates a test tube containing the sample liquid 27a therein. The presence or absence of the test tube 25 is monitored by receptacle detection means 37. The reference numeral 21 denotes a washing waste liquid receiver. The washing waste liquid which has flowed back through and washed the sample suction tube 17 is directed to the waste liquid receptacle 5 by a waste liquid tube 22.

Description will now be made of the operational process of sample supplying in the above-described construction.

In the initial state, the interiors of the pumps 1, 2, 3, the 3-port valves 6, 7, 8, the tubes 9, 10, 11, 12, 13, 14, 17, 18, the 6-port valve 15 and the sample loop 16 are all filled with the sheath liquid.

Figure 3:
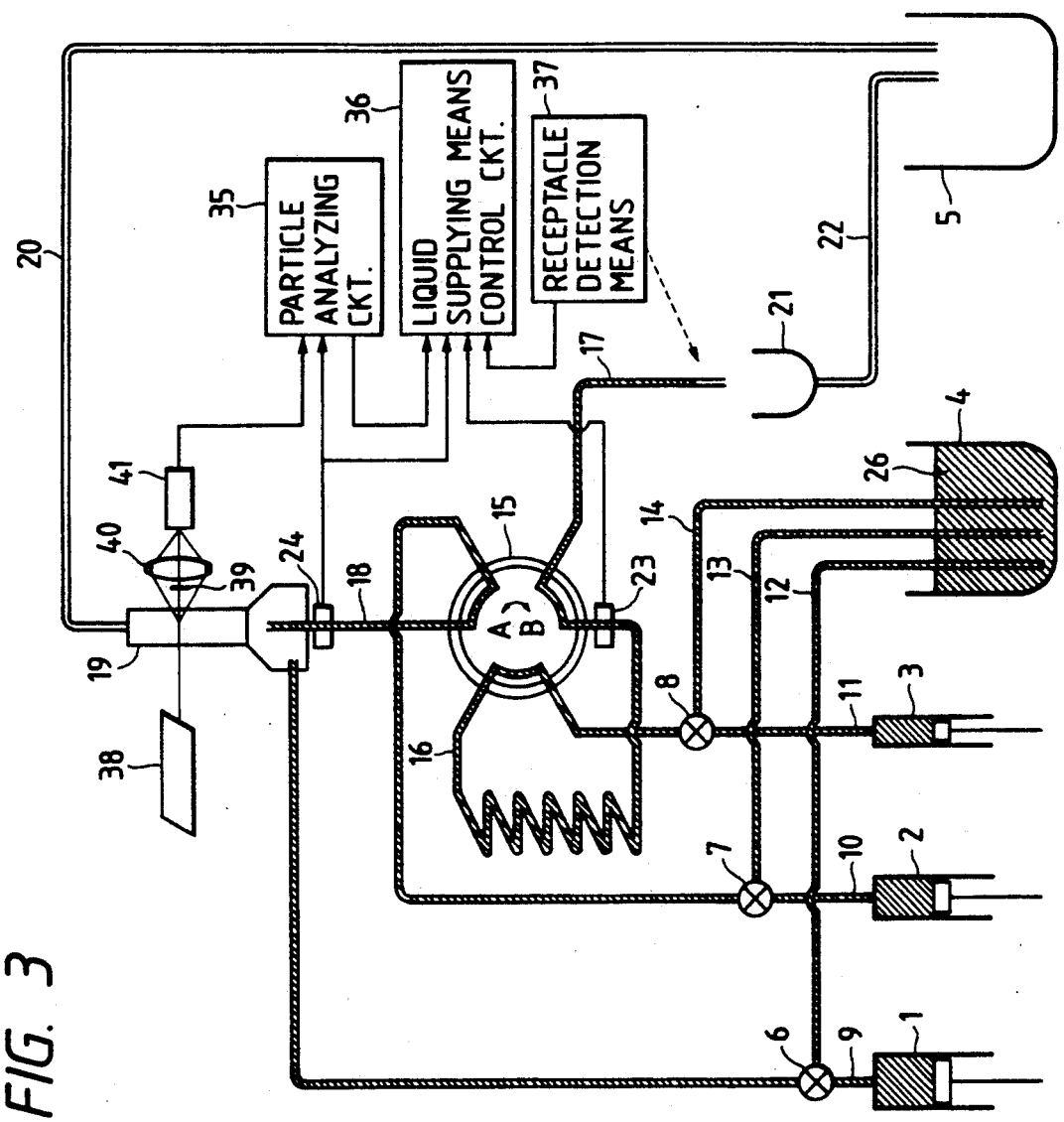
FIG. 3 is a schematic illustration showing a first step of the embodiment.
Figure 4:
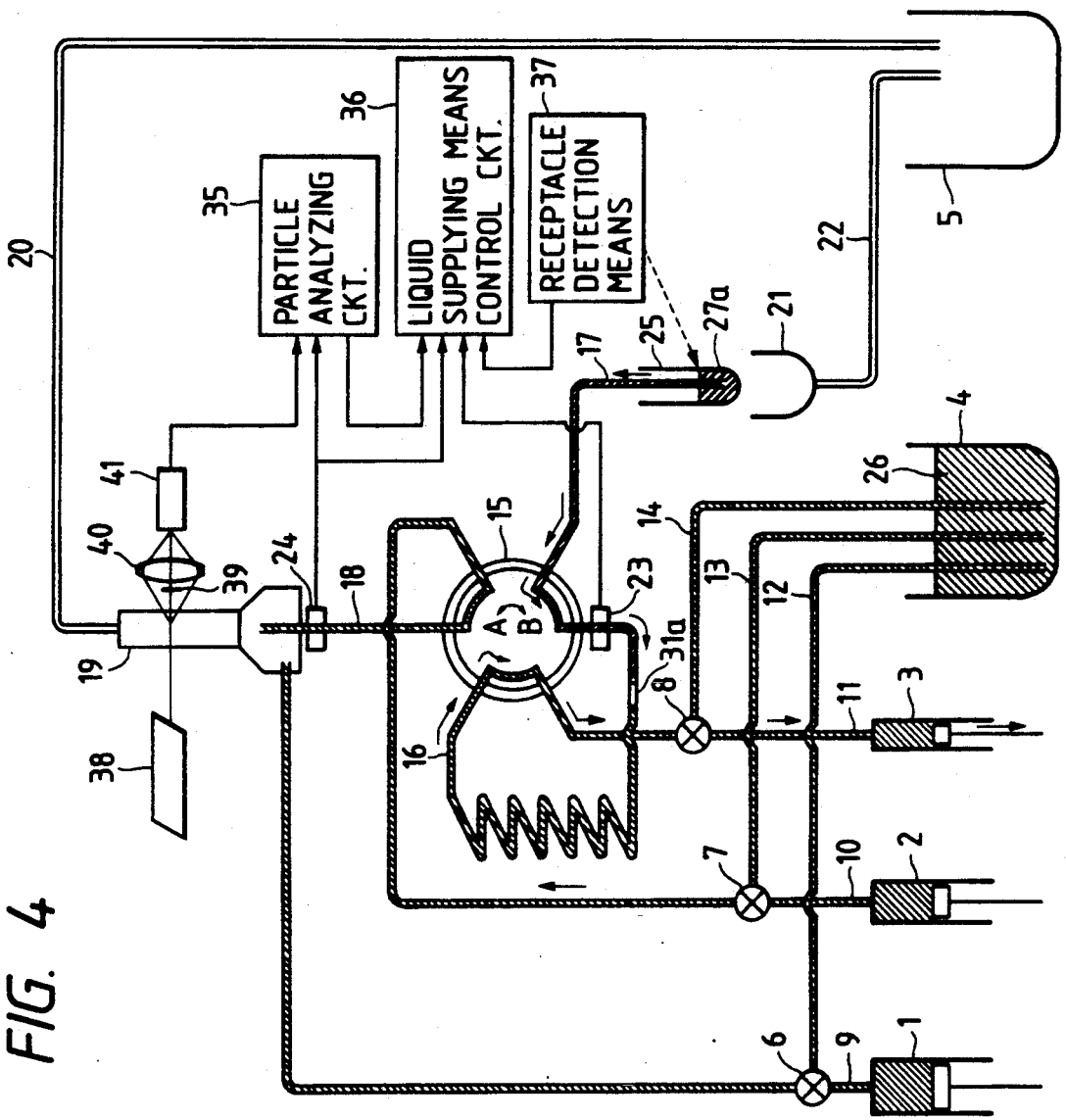
FIG. 4 is a schematic illustration showing a further step of the embodiment.

In the sample sucking step, the 6-port valve 16 first assumes a position shown in FIG. 3, and the sample pump 3 performs its sucking operation and waits with a small amount of air sucked from the fore end of the suction tube 17. Subsequently, when as shown in FIG. 4, the operator brings the sample liquid receptacle 25 containing therein the sample liquid 27a such as a blood sample or coagulated latex suspension to the position of the suction tube 17 and pushes a suction starting button provided on the apparatus body, the sample pump performs its sucking operation and a predetermined amount of sample liquid is sucked into the suction tube 17, whereafter the operation is stopped. Here, the small amount of air previously sucked in becomes an air layer 31a which plays the role of separating the sheath liquid and the sample liquid from each other. If during the suction, the sample liquid 27a should become exhausted or by mistake, the fore end of the suction tube 17 should come out from the surface of the sample liquid and suck air thereinto, the sensor 23 detects the air and a signal is sent to the liquid supplying means control circuit 36, whereby the sucking operation may be forcibly stopped. That is, even when during the supply of the sample, air is fed into the sample tube due to some accident or other, the fact that air has been fed into the sample tube is detected and the feeding operation is stopped and thus, safety becomes higher. Design is made such that the sucking operation is not stopped by the first air layer 31a passing through the sensor 23.

Figure 5:
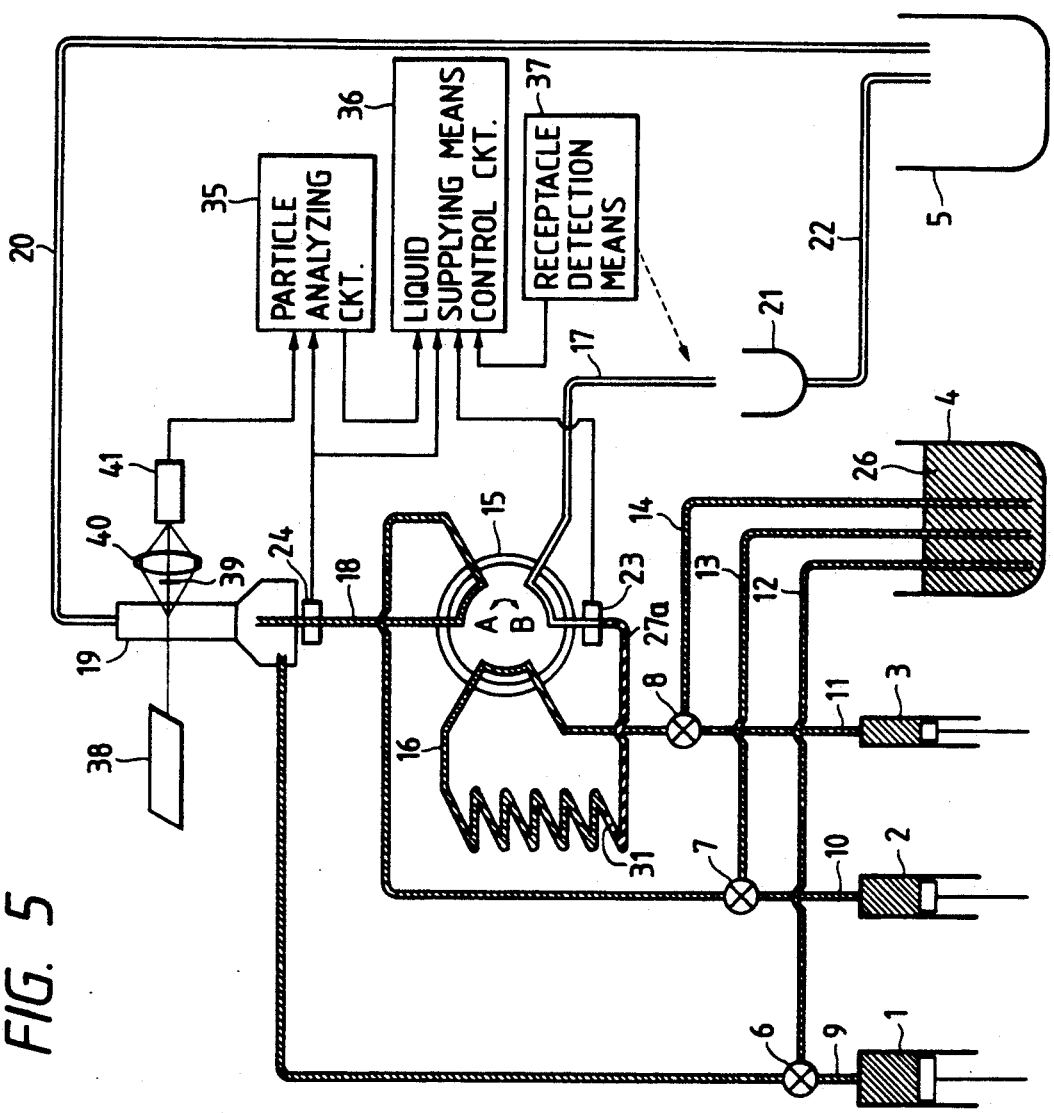
FIG. 5 is a schematic illustration showing a further step of the embodiment.

When the suction of a predetermined amount of sample liquid from the sample liquid receptacle 25 is terminated and the operator removes the sample liquid receptacle 25, the receptacle detection means 37 sends a signal to the liquid supplying means control circuit 36, and the sample pump 3 again starts suction to supply the sample liquid remaining in the suction tube 17 into the sample loop. At this time, air is sucked from the fore end of the suction tube 17, and when as shown in FIG. 5, the air reaches the position of the sensor 23, the sucking operation of the sample pump 3 is stopped by the signal of the sensor 23.

Figure 6:
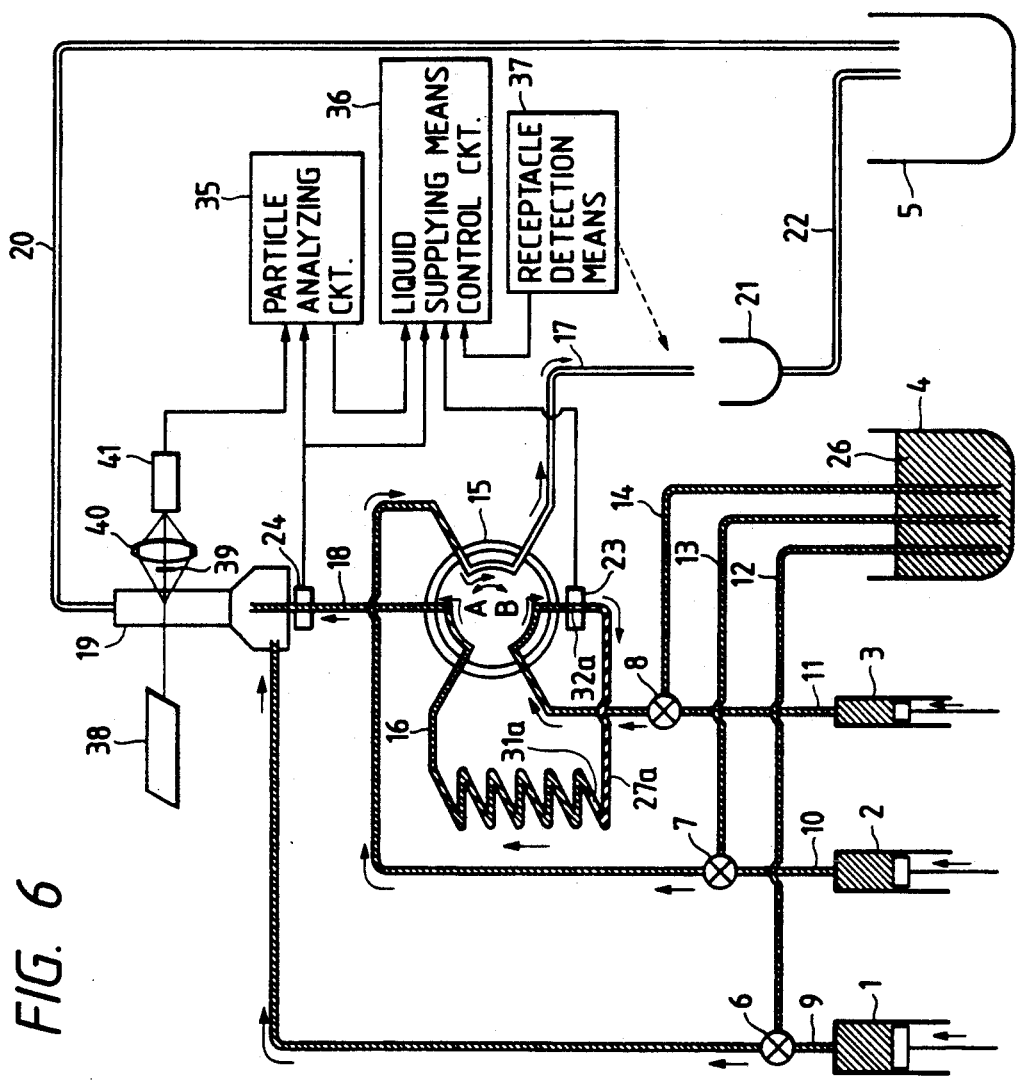
FIG. 6 is a schematic illustration showing a further step of the embodiment.

Subsequently, the 6-port valve 15 rotates in the direction of arrow A and the connection of the water channel changes as shown in FIG. 6. Here, the sample pump 3 performs the operation of supplying a predetermined amount of liquid and advances the previously sucked sample liquid by the sheath liquid with the air layer 32a interposed therebetween. The sheath liquid and the sample liquid are separated from each other, without being mixed together, by the air layer 32a existing between the sheath liquid and the sample liquid.

At this time, the washing pump 2 pushes out the sheath liquid by the liquid supplying operation, and a part of the interior of the 6-port valve 15 and the interior of the sample suction tube 17 are washed by the sheath liquid being caused to flow back therethrough. The waste liquid used for washing is discharged into the waste liquid receiver 21 and discharged into the waste liquid receptacle 5 through the waste liquid tube 22.

When a predetermined amount of sample liquid is advanced by the sample pump 3 with the aid of the sheath liquid, the liquid supplying operation is stopped and the washing by the liquid supplying operation of the washing pump 2 is also stopped.

Figure 9:
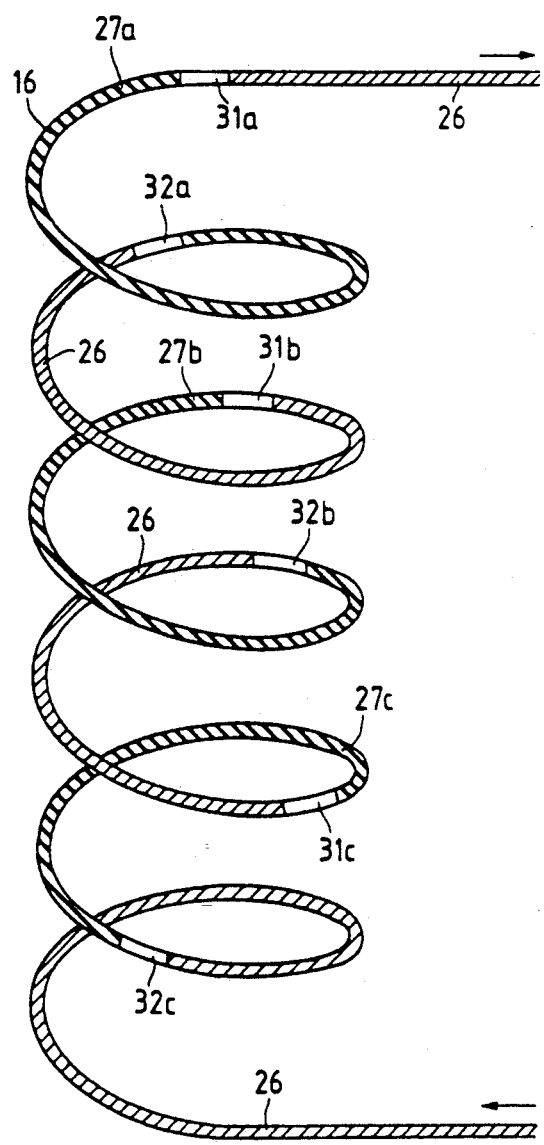
FIG. 9 is a detailed view of a sample loop.
Figure 7:
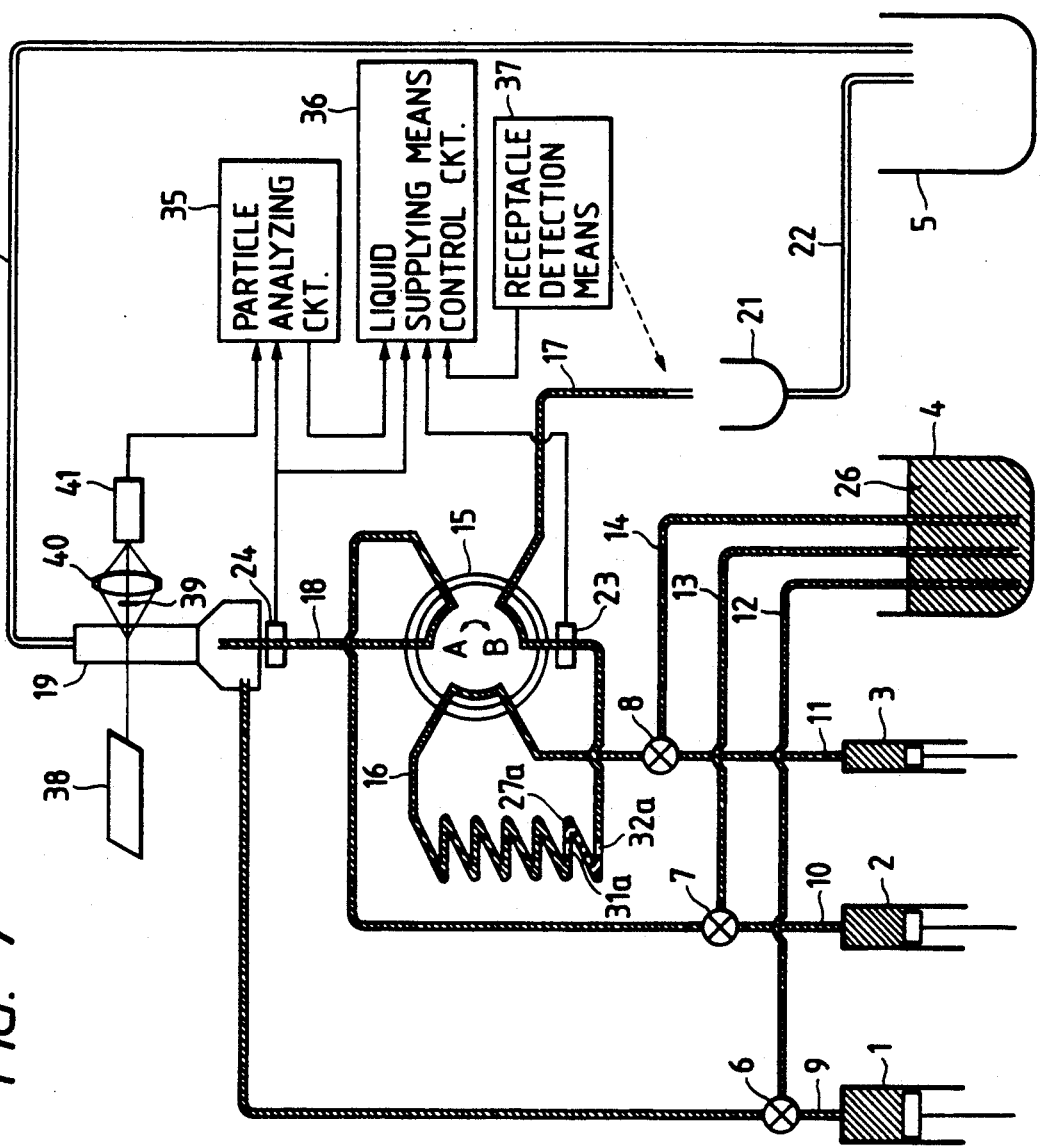
FIG. 7 is a schematic illustration showing a further step of the embodiment.

The 6-port valve 15 then rotates in the direction of arrow B and the connection of the water channel changes over as shown in FIG. 7. The sample pump 3 sucks a small amount of air from the fore end of the suction tube 17 and waits, and can shift to the step of sucking the next sample liquid. As a similar step is repeated to thereby suck a plurality of kinds of sample liquids one after another, the sheath liquid 26 and the sample liquids 27a, 27b, 27c are successively accumulated in the sample loop 16 while being spaced apart from one another by air layers 31a, 32a, 31b, 32b, 31c, 32c, as shown in FIG. 9. The material of the sample loop 16 is fluorine resin which easily repels liquid, and after the flow of the sample liquid, the sheath liquid spaced apart by the air layer and having the washing function flows to wash the sample loop and therefore, different kinds of samples do not mix with one another.

The number of sample liquids which can be sucked and accumulated at a time is determined by the amount of sample liquids sucked, the amount of sheath liquid sucked, and the volume of the sample loop 16, i.e., the inner diameter and length of the sample loop 16. The frequency of suction of the samples is counted by the liquid supplying means control circuit 36, and when a predetermined frequency of suction is reached, control is effected so that the sucking operation takes place no longer.

Figure 8:
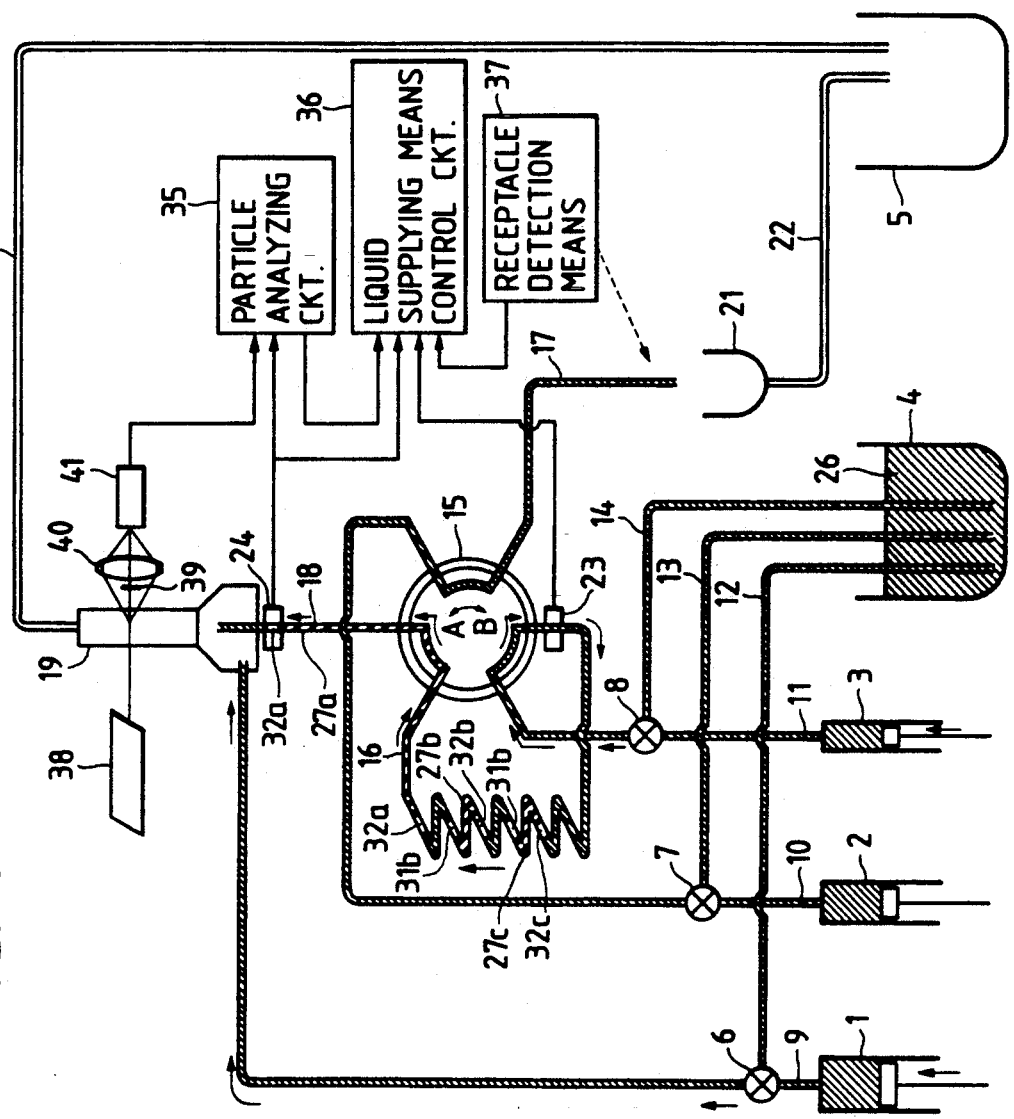
FIG. 8 is a schematic illustration showing a further step of the embodiment.

When the accumulation of a plurality of sample liquids into the sample loop is terminated in the manner described above, the apparatus assumes the measurement start waiting state as shown in FIG. 8, and by the operator depressing a measurement start button provided on the apparatus body, measurement of the sample liquids is started. Even if a prescribed number of kinds of sample liquids are not accumulated in the sample loop 16, measurement can be started by depressing the measurement start button.

When the measurement start button is depressed, the sheath pump 1 first supplies the sheath liquid to the flow cell 19 and forms a layer flow of the sheath liquid in the flow cell 19. At the same time, the sample pump 3 moves the syringe at a high speed and effects the fast supply of the sheath liquid in the sample loop 16. The fast supply is effected to rapidly pass the sheath liquid which has nothing to do with measurement and shorten the total measurement time as much as possible. As shown in FIG. 8, the air layer 31a reaches the sensor 24, and the output signal of the sensor is sent to the particle analyzing circuit 35 and the liquid supplying means control circuit 36. In response to the signal of the sensor 24, the sample pump 3 moves the syringe at a normal speed by the liquid supplying means control circuit 36 so that the sample liquid may assume an appropriate flow diameter in the flow cell portion, and applies proper pressure to the interior of the sample loop. Also, the particle analyzing circuit 35 begins to introduce data thereinto after the flow of the sample becomes stable in a predetermined time after the signal of the sensor 24.

Usually, the introduction of data is terminated after it has been effected for a set number of particles or for a predetermined time, but if during the introduction of data, the air layer 32a between the sample liquid 27a and the sheath liquid pushing it out passes the sensor 24, the signal of the sensor 24 is sent to the particle analyzing circuit 35 and the introduction of data is forcibly terminated.

When the introduction of data is terminated, recording of the introduced data onto a recording medium is started and at the same time, a signal is sent from the particle analyzing circuit 35 to the liquid supplying means control circuit 36, and the sample pump 3 moves the syringe at a high speed to pressurize the interior of the sample loop 16 to high pressure, and the fast supply of the sheath liquid for washing is effected to thereby effect the washing of the tube 18 and the flow cell 19 quickly. When the air layer 31b in the sample loop reaches the sensor 24, the sample pump 3 is stopped, whereby the liquid supplying operation is stopped. When the recording of the introduced data which is being effected at the same time is terminated, a signal is sent from the particle analyzing circuit 35 to the liquid supplying means control circuit 36, and the sample pump 3 resumes the supply of the next sample liquid at a normal supply speed.

By the repetition of what has been described above, measurements of a plurality of kinds of sample liquids are automatically effected one after another. When the introduction of the data of the last sample liquid 27c is terminated, a signal is sent from the particle analyzing circuit 35 to the liquid supplying means control circuit 36, and the sheath liquid is extruded by the sample pump 3 to wash the water channel, whereafter the apparatus is stopped from operating. Various methods of effecting particle analysis by the use of the histogram or cytogram process on the basis of the thus obtained measurement data are well known, and the calculation thereof is effected by the particle analyzing circuit 35.

While the present invention has been described with respect to an embodiment in which the present invention is applied to a flow cytometer, the present invention is not restricted thereto, but can be widely applied to apparatuses in which samples are successively supplied to an inspecting portion and inspected thereby, such as particle counters, Colter measuring apparatus for effecting measurement of fine particles from the electrical impedance of an inspecting portion, or particle measuring apparatuses using photosounds.

As described above, according to the present invention, it becomes possible to measure a plurality of kinds of samples efficiently. Also, by increasing the supply speed of the extrusion liquid during the time other than the measurement of the samples, the washing time and the supply time can be shortened. Thereby, the measurement cycle can be shortened when a plurality of samples are continuously repetitively measured, and the processing ability per unit time can be enhanced.

Further, according to the present invention, the operator performs the operation of introducing samples in a lump at first, whereafter continuous measurement is effected automatically and therefore, the operator can do other work during the continuous measurement, and this means the advantage that the working efficiency to the operator is enhanced.

I claim:

1. A sample inspecting method, comprising the steps of:
   serially accumulating a first sample, a washing liquid, and a second sample into a liquid path;
   serially supplying the accumulated liquids to an inspecting station by pressurizing the liquid path;
   serially inspecting the first sample at a liquid path inspecting portion, washing the liquid path inspecting portion with the washing liquid and inspecting the second sample at the liquid path inspecting portion; and
   detecting a boundary between the first and second sample liquids and the washing liquid at a predetermined portion in the liquid path to discriminate between the sample inspection operation and the washing operation, wherein
   the pressure applied to the liquid path is changed between the sample inspection operation and the washing operation.

2. A sample inspecting method according to claim 1, further comprising the step of incorporating a gas between each of the accumulated liquids to separate the liquids from each other.

3. A sample inspecting method according to claim 2, wherein the boundary between the first and second sample liquids and the washing liquid is detected by detecting the gas incorporated between each liquid.

4. A sample inspecting method according to claim 1, wherein the first and second sample liquids are optically inspected.

5. A sample inspecting apparatus, comprising:
   accumulation means for serially accumulating a first sample, a washing liquid, and a second sample into a liquid path;
   pressurizing means for serially supplying the accumulated liquids to an inspecting portion by pressurizing the liquid path;
   inspecting means, disposed along the liquid path, for performing a sample inspection operation of the first sample and the second sample at the inspecting portion;
   control means for regulating the pressure supplied by said pressurizing means, wherein the pressure supplied during the sample inspection operation is different from the pressure supplied at other operations; and
   detection means provided at a predetermined portion in the liquid path for detecting a boundary between the sample liquids and the washing liquid and for discrimination between the sample inspection operation and other operations on the basis of an output of said detection means.

6. A sample inspecting apparatus according to claim 5, wherein said accumulating means incorporates a gas between each of the accumulated liquids.

7. A sample inspecting apparatus according to claim 6, wherein said detection means includes a light source and a light detector located on opposite sides of the liquid path, wherein the gas incorporated between the liquids is detected by an output of said detection means.

8. A sample inspecting apparatus according to claim 7, wherein said light source is a laser.

9. A sample inspecting apparatus according to claim 5, wherein said inspecting means includes optical means for optically inspecting the sample liquids.

10. A flow cytometer, comprising:
sample tube means for serially accumulating a first sample containing particles to be examined, a washing liquid, and a second sample containing particles to be examined in a liquid path;
pressurizing means for pressurizing said sample tube to transfer the accumulated liquids;
flow cell means, connected to said sample tube means, for isolating the particles in the first and second samples to be measured;
irradiating optical means including a light source for applying a measuring light beam to the isolated particles in said flow cell;
measuring optical means including a light detector for receiving the measuring light beam from the particles flowing through said flow cell;
analyzing means for inspecting the particles contained in said first and second samples during a sample inspection operation on the basis of an output of said light detector;
control means for regulating the pressure supplied by said pressurizing means, wherein the pressure supplied during the sample inspection operation is different from the pressure supplied at other operations; and
detection means provided at a predetermined portion in the liquid path for detecting a boundary between the sample liquids and the washing liquid and for discriminating between the sample inspection operation and other operations on the basis of an output of said detection means.

11. A flow cytometer according to claim 10, further comprising means for introducing a sheath liquid into said flow cell, wherein the isolated particles are surrounded by the sheath liquid and flow one by one through said flow cell.

12. A flow cytometer according to claim 10, wherein said light source is a laser.

13. A flow cytometer according to claim 10, wherein the light measure by said measuring optical means is either one or both of a scattered light and a fluorescence light reflected from the particles.

14. A flow cytometer according to claim 10, wherein said first and second samples are sample liquids containing cell particles.

* * * * *

UNITED STATES PATENT AND TRADEMARK OFFICE
CERTIFICATE OF CORRECTION

PATENT NO. : 5,134,445
DATED      : July 28, 1992
INVENTOR(S) : Yoshiyuki Toge

It is certified that error appears in the above-identified patent and that said Letters Patent is hereby corrected as shown below:

On the title page, Item:

[56] REFERENCES CITED:

U.S. PATENT DOCUMENTS, "3,418,053  12/1968  Pelaoin" should read
--3,418,053  12/1968  Pelavin--.

COLUMN 2:

Line 27, "and 8," should read --7 and 8,--.

Signed and Sealed this

Twenty-sixth Day of October, 1993

Attest:

Attesting Officer

BRUCE LEHMAN

Commissioner of Patents and Trademarks